(12) United States Patent
Witham et al.

(10) Patent No.: US 11,957,646 B2
(45) Date of Patent: Apr. 16, 2024

(54) METHODS AND COMPOSITIONS OF STABLE PHENYLEPHRINE FORMULATIONS

(71) Applicant: Paragon BioTeck, Inc., Portland, OR (US)

(72) Inventors: Patrick H. Witham, Eugene, OR (US); Sailaja Machiraju, Beaverton, OR (US); Lauren Mackensie-Clark Bluett, Milwaukie, OR (US)

( * ) Notice: Subject to any disclaimer, the term of this patent is extended or adjusted under 35 U.S.C. 154(b) by 0 days.

(21) Appl. No.: 16/673,721

(22) Filed: Nov. 4, 2019

(65) Prior Publication Data

US 2020/0085766 A1 Mar. 19, 2020

Related U.S. Application Data

(63) Continuation of application No. 15/625,624, filed on Jun. 16, 2017, now abandoned, which is a continuation of application No. 14/477,718, filed on Sep. 4, 2014, now abandoned, which is a continuation of application No. 14/080,771, filed on Nov. 14, 2013, now Pat. No. 8,859,623.

(51) Int. Cl.
| | |
|---|---|
| *A61K 31/137* | (2006.01) |
| *A61K 9/00* | (2006.01) |
| *A61K 47/02* | (2006.01) |
| *A61P 27/08* | (2006.01) |

(52) U.S. Cl.
CPC .......... *A61K 31/137* (2013.01); *A61K 9/0048* (2013.01); *A61K 47/02* (2013.01); *A61P 27/08* (2018.01)

(58) Field of Classification Search
CPC ...... A61K 31/137; A61K 9/0048; A61P 27/08
See application file for complete search history.

(56) References Cited

U.S. PATENT DOCUMENTS

| | | |
|---|---|---|
| 4,260,600 A | 4/1981 | Valle |
| 8,859,623 B1 | 10/2014 | Witham et al. |
| 2003/0119915 A1 | 6/2003 | Booth et al. |
| 2011/0104273 A1 | 5/2011 | Hou |
| 2012/0149073 A1 | 6/2012 | Alvizo et al. |
| 2014/0023569 A1 | 1/2014 | Schoeppe et al. |
| 2015/0133563 A1 | 5/2015 | Witham et al. |
| 2018/0036328 A1 | 2/2018 | Tsubota et al. |

FOREIGN PATENT DOCUMENTS

WO    WO-2009074853 A2 *   6/2009   ........... A61K 31/137

OTHER PUBLICATIONS

Akorn, "Phenylephrine Hydrochloride Ophthalmic Solution, USP 2.5%(10%)—Sterile", Rev. Jul. 2011 (Year: 2011).*

(Continued)

*Primary Examiner* — Bethany P Barham
*Assistant Examiner* — Barbara S Frazier
(74) *Attorney, Agent, or Firm* — Andrew J. Anderson, Esq.; Harter Secrest & Emery LLP (57) ABSTRACT

The invention is directed to methods and compositions of stabilizing phenylephrine formations. The composition has good time-dependent stability at low temperature and has no change in its outward appearance even after having been stored at least 6 months.

18 Claims, 4 Drawing Sheets

(56) References Cited

OTHER PUBLICATIONS

Case No. PRG2015-00011 Exhibit 2023 Sterile Phenylephrine Hydrochloride Opthalmic Solution 2.5% USP Rx Only, distributed by HUB Pharmaceuticals, LLC. U.S. National Library of Medicine, http://dailymed.nlm.nih.gov/dailymed/drugInfo.cfm?setid=21525f9e-f3a2-4871-81bf-90a0686968f0 (last visited Feb. 5, 2016)—Redacted Patent Owner's Preliminary Response Pursuant to 37 C.F.R. § 42.207 dated Feb. 10, 2016 (6 pgs.).
Case No. PRG2015-00011 Exhibit 2025 ATCC, Product sheet for *Bacillus subtilis* subsp. *Subtilis* (ATCC® 6051TM) (2013)—Redacted Patent Owner's Preliminary Response Pursuant to 37 C.F.R. § 42.207 dated Feb. 10, 2016 (2 pgs.).
Case No. PRG2015-00011 Exhibit 2026 ATCC, Product sheet for Aspergillus fumigatus (ATCC® 1022TM) (2016)—Redacted Patent Owner's Preliminary Response Pursuant to 37 C.F.R. § 42.207 dated Feb. 10, 2016 (2 pgs.).
Case No. PRG2015-00011 Exhibit 2028 ATCC, Product sheet for *Staphylococcus aureus* subsp. *Aureus* (ATCC® 12600TM) (2014)—Redacted Patent Owner's Preliminary Response Pursuant to 37 C.F.R. § 42.207 dated Feb. 10, 2016 (2 pgs.).
Case No. PRG2015-00011 Exhibit 2029 Food and Drug Administration, Appendix 4: Bacterial Pathogen Growth and Inactivation, http://www.fda.gov/downloads/Food/GuidanceRegulation/UCM25244 7.pdf (last visited Feb. 3, 2016)—Redacted Patent Owner's Preliminary Response Pursuant to 37 C.F.R. § 42.207 dated Feb. 10, 2016 (22 pgs.).
Case No. PRG2015-00011 Exhibit 2033 Letter to the Honorable Leonard D. Wexler from counsel to Altaire Pharmaceuticals, Inc. and Sawaya Aquebogue, LLC, Case 2:15-cv-02416-LDW-AYS, Document 34, Filed Oct. 15, 2015 in the Eastern District of New York—Redacted Patent Owner's Preliminary Response Pursuant to 37 C.F.R. § 42.207 dated Feb. 10, 2016 (1 pg.).
Case No. PRG2015-00011 Exhibit 2037 Sigma-Aldrich® catalog entries for phenylephrine hydrochloride, http://www.sigmaaldrich.com/catalog/search?interface=All&term=phe nylephrine&N=0&mode=match+partialmax&focus=product&lang=en &region=US (last visited Feb. 7, 2016)—Redacted Patent Owner's Preliminary Response Pursuant to 37 C.F.R. § 42.207 dated Feb. 10, 2016 (3 pgs.).
Case No. PRG2015-00011 Exhibit 2039 Image of Drs. Steeg and Reuter Optical Polarimeter Model SR-6 obtained from, http://easytechsell.com/products/polyscience-sr6-fc-polarimeter-full-circle-scale-sr-6-steeg-reuter-warranty-free-domestic-shipping (last visited Feb. 8, 2016)—Redacted Patent Owner's Preliminary Response Pursuant to 37 C.F.R. § 42.207 dated Feb. 10, 2016 (4 pgs.).
Case No. PRG2015-00011 Exhibit 2040 HPLC chromatograms obtained by Paragon for phenylephrine hydrochloride enantiomers and controls run under the USP Compendium method, Project Name: PPHcl_NasalJ_Sys4_160118_NJ (2016)—Redacted Patent Owner's Preliminary Response Pursuant to 37 C.F.R. § 42.207 dated Feb. 10, 2016 (5 pgs.).
Case No. PRG2015-00011 Exhibit 2041 Declaration of Patrick Witham in Support of Paragon's Motion to Seal Paper 20 and Exhibit 2034—Paragon's Motion to Seal Paper 20 and Exhibit 2034 dated Apr. 12, 2016 (3 pgs.).
Case No. PRG2015-00011 Exhibit 2042 Email from Michael T. Rosato to the Patent Trial and Appeal Board, May 12, 2016—Paragon's Identification of Improper New Reply Materials That Should Be Struck From the Record dated May 20, 2016 (2 pgs.).
Case No. PRG2015-00011 Final Written Decision under U.S.C. § 328(a) and 37 C.F.R. § 42.73 entered Nov. 14, 2016 (Paper No. 48) (21 pgs.).
Case No. PRG2015-00011 Joint Motion to Preserve the Record Pending Appeal dated Dec. 23, 2016 (5 pgs.).
Case No. PRG2015-00011 Joint Stipulation to Extend Due Dates 1 & 2 dated Jan. 28, 2016 (3 pgs.).
Case No. PRG2015-00011 Order Conduct of the Proceeding entered Apr. 1, 2016 (Paper No. 29) (5 pgs.).
Case No. PRG2015-00011 Order Conduct of the Proceeding entered Apr. 11, 2016 (Paper No. 31) (3 pgs.).
Case No. PRG2015-00011 Order conduct of the Proceeding entered Apr. 8, 2016 (Paper No. 30) (3 pgs.).
Case No. PRG2015-00011 Order Conduct of the Proceeding entered May 18, 2016 (Paper No. 38) (6 pgs.).
Case No. PRG2015-00011 Order Conduct of the Proceeding entered Sep. 14, 2015 (3 pgs.) (Paper No. 8).
Case No. PRG2015-00011 Order Granting Request for Oral Argument entered Jul. 1, 2016 (Paper No. 44) (4 pgs.).
Case No. PRG2015-00011 Order Joint Motion to Preserve the Record Pending Appeal entered Jan. 9, 2016 (Paper No. 50) (4 pgs.).
Case No. PRG2015-00011 Paragon's Identification of Improper New Reply Materials that Should Be Struck From the Record dated May 20, 2016 (10 pgs.).
Case No. PRG2015-00011 Paragon's Motion to Seal Paper 20 and Exhibit 2034 dated Apr. 12, 2016 (13 pgs.).
Case No. PRG2015-00011 Paragon's Objections to Untimely Reply Evidence dated May 13, 2016 (5 pgs.).
Case No. PRG2015-00011 Paragon's Reply in Support of Its Identification of Improper New Reply Materials That Should Be Struck From the Record dated Jun. 2, 2016 (5 pgs.).
Case No. PRG2015-00011 Patent Owner Paragon Bioteck, Inc.'s Power of Attorney dated May 29, 2015 (2 pgs.).
Case No. PRG2015-00011 Patent Owner's Motion to Seal and Motion for Entry of Protective Order Pursuant to 37 C.F.R. §42.14 and §42.54 dated Aug. 24, 2015 (8 pgs.).
Case No. PRG2015-00011 Patent Owner's Preliminary Response Pursuant to 37 C.F.R. §42.207 dated Aug. 24, 2015 (44 pgs.).
Case No. PRG2015-00011 Patent Owner's Request for Oral Argument Pursuant to 37 C.F.R. §42.70 dated Jun. 3, 2016 (3 pgs.).
Case No. PRG2015-00011 Petition for Post-Grant Review of U.S. Pat. No. 8,859,623 filed May 11, 2015 (78 pgs.).
Case No. PRG2015-00011 Petitioner's Motion to Seal dated May 6, 2016 (7 pgs.).
Case No. PRG2015-00011 Petitioner's Motion to Seal dated Feb. 29, 2016 (12 pgs.).
Case No. PRG2015-00011 Petitioner's Motion to Seal dated Sep. 28, 2015 (4 pgs.).
Case No. PRG2015-00011 Petitioner's Request for Oral Argument dated Jun. 3, 2016 (3 pgs.).
Case No. PRG2015-00011 Petitioner's Response to Patent Owner's Identification of Alleged Improper Reply Evidence dated May 27, 2016 (5 pgs.).
Case No. PRG2015-00011 Power of Attorney Per C.F.R. §42.10(b) dated Feb. 18, 2016 (2 pgs.).
Case No. PRG2015-00011 Power of Attorney Per C.F.R. §42.10(b) dated May 11, 2015 (2 pgs.).
Case No. PRG2015-00011 Proceedings held Jul. 12, 2016 *Altair Pharmaceuticals, Inc.* (Petitioner) v. *Paragon Bioteck, Inc.* (Patent Owner) (Paper No. 47) (Aug. 10, 2016) (52 pgs.).
Case No. PRG2015-00011 Scheduling Order entered Nov. 16, 2015 (Paper No. 15) (7 pgs.).
Millard et al. The Stability of Aqueous Solutions of Phenylephrine at Elevated Temperatures: Identification of the Decomposition Products. J. Pharm. Pharmac. 1973. 25(Suppl):24P-31P.
Altaire, Altafrin 2.5% Phenylephrine Hydrochloride Ophthalmic Solution USP, 2.5%, rev. Aug. 2005 (2005).
Case No. PRG2015-00011 Decision on Petitioner's Motion to Seal entered Jul. 5, 2016 (Paper No. 45) (3 pgs.).
Case No. PRG2015-00011 Decision on Petitioner's Motion to Seal entered Jul. 5, 2016 (Paper No. 46) (4 pgs.).
Case No. PRG2015-00011 Decision Patent Owner's Motion to Seal and for Entry of Protective Order entered Oct. 26, 2015 (Paper No. 12) (3 pgs.).
Case No. PRG2015-00011 Decision Petitioner's Motion to Seal entered Mar. 29, 2016 (Paper No. 27) (6 pgs.).
Case No. PRG2015-00011 Decision Petitioner's Motion to Seal entered Oct. 26, 2015 (Paper No. 13) (3 pgs.).
Case No. PRG2015-00011 Due Date Appendix (1 pg.).
Case No. PRG2015-00011 Exhibit 1001 U.S. Pat. No. 8,859,623—Petition for Post-Grant Review of U.S. Pat. No. 8,859,623 filed May 11, 2015 (12 pgs.).

(56) References Cited

OTHER PUBLICATIONS

Case No. PRG2015-00011 Exhibit 1002 Prosecution and Transaction History of U.S. Pat. No. 8,859,623—Petition for Post-Grant Review of U.S. Pat. No. 8,859,623 filed May 11, 2015 (617 pgs.).
Case No. PRG2015-00011 Exhibit 1003 Sawaya Declaration—Petition for Post-Grant Review of U.S. Pat. No. 8,859,623 filed May 11, 2015 (30 pgs.).
Case No. PRG2015-00011 Exhibit 1004 Altafrin 2.5% Product Label (Rev. Aug. 2005)—Petition for Post-Grant Review of U.S. Pat. No. 8,859,623 filed May 11, 2015 (1 pg.).
Case No. PRG2015-00011 Exhibit 1005 Altafrin 10% Product Label (Rev. Nov. 2004)—Petition for Post-Grant Review of U.S. Pat. No. 8,859,623 filed May 11, 2015 (1 pg.).
Case No. PRG2015-00011 Exhibit 1006 Neofrin 2.5% Lot 12402 Product Images (Oct. 2012)—Petition for Post-Grant Review of U.S. Pat. No. 8,859,623 filed May 11, 2015 (3 pgs.).
Case No. PRG2015-00011 Exhibit 1007 OCuSOFT, Inc. Invoice (Oct. 2012)—Petition for Post-Grant Review of U.S. Pat. No. 8,859,623 filed May 11, 2015 (1 pg.).
Case No. PRG2015-00011 Exhibit 1008 Phenylephrine Hydrochloride Ophthalmic Solution, USP 10% Product Images (Expiration Dec. 2013)—Petition for Post-Grant Review of U.S. Pat. No. 8,859,623 filed May 11, 2015 (3 pgs.).
Case No. PRG2015-00011 Exhibit 1009 Hub Pharmaceuticals Invoice (Oct. 2012)—Petition for Post-Grant Review of U.S. Pat. No. 8,859,623 filed May 11, 2015 (1 pg.).
Case No. PRG2015-00011 Exhibit 1010 FDA Information Request (Dec. 2012)—Petition for Post-Grant Review of U.S. Pat. No. 8,859,623 filed May 11, 2015 (4 pgs.).
Case No. PRG2015-00011 Exhibit 1011 U.S. Pat. No. 3,966,749 (Issued Jun. 29, 1976)—Petition for Post-Grant Review of U.S. Pat. No. 8,859,623 filed May 11, 2015 (7 pgs.).
Case No. PRG2015-00011 Exhibit 1012 Identification Study for the Racemic(-) Form of Phenylephrine Hydrochloride in Phenylephrine Hydrochloride Ophthalmic Solution, USP 2.5% and 10% (STU0328) (Feb. 2013)—Petition for Post-Grant Review of U.S. Pat. No. 8,859,623 filed May 11, 2015 (9 pgs.).
Case No. PRG2015-00011 Exhibit 1013 Paragon Bioteck, Inc. Purchase Order # 4009 (Apr. 2013)—Petition for Post-Grant Review of U.S. Pat. No. 8,859,623 filed May 11, 2015 (1 pg.).
Case No. PRG2015-00011 Exhibit 1014 Paragon Bioteck, Inc. Purchase Order # 4010 (Jul. 2013)—Petition for Post-Grant Review of U.S. Pat. No. 8,859,623 filed May 11, 2015 (1 pg.).
Case No. PRG2015-00011 Exhibit 1015 Akorn Phenylephrine 2.5% (Lot 091281) and 10 % (Lot 081431) Chromatograms—Petition for Post-Grant Review of U.S. Pat. No. 8,859,623 filed May 11, 2015 (2 pgs.).
Case No. PRG2015-00011 Exhibit 1016 Altaire Pharmaceuticals, Inc. Phenylephrine 2.5% (Lots 11302, 11577, 11578) and 10 % (Lots 11323, 11581, 11582) Chromatograms—Petition for Post-Grant Review of U.S. Pat. No. 8,859,623 filed May 11, 2015 (2 pgs.).
Case No. PRG2015-00011 Exhibit 1017 Altaire Pharmaceuticals, Inc. Phenylephrine 2.5% (Lot 15040) Elevated Temperature Storage Chromatograms—Petition for Post-Grant Review of U.S. Pat. No. 8,859,623 filed May 11, 2015 (2 pgs.).
Case No. PRG2015-00011 Exhibit 1018 Altaire Pharmaceuticals, Inc. Phenylephrine Product Insert (Aug. 2010)—Petition for Post-Grant Review of U.S. Pat. No. 8,859,623 filed May 11, 2015 (2 pgs.).
Case No. PRG2015-00011 Exhibit 1019 Summary of Chiral Purity Testing by HPLC of Phenylephrine HCl Ophthalmic Solution USP (2.5% and 10%) (Apr. 2015)—Petition for Post-Grant Review of U.S. Pat. No. 8,859,623 filed May 11, 2015 (1 pg.).
Case No. PRG2015-00011 Exhibit 1020 Drug Substances used in the Manufacture of Phenylephrine HCL Ophthalmic Solution (Apr. 2015)—Petition for Post-Grant Review of U.S. Pat. No. 8,859,623 filed May 11, 2015 (1 pg.).
Case No. PRG2015-00011 Exhibit 1021 *Kapsch Trafficcom IVHS Inc.* v. *Neology, Inc.,* IPR2015-00808, at 4 (Paper No. 13) (P.T.A.B. Sep. 14, 2015)—Redacted Reply to Patent Owner's Preliminary Statement dated Sep. 28, 2015 (21 pgs).
Case No. PRG2015-00011 Exhibit 1024 Declaration of M. Sawaya dated Feb. 26, 2017—Petitioner's Motion to Seal dated Feb. 29, 2016 (5 pgs.).
Case No. PRG2015-00011 Exhibit 1025 Declaration No. 3 of Assad Sawaya (May 4, 2016)—Petitioner's Reply to Patent Owner's Response dated May 6, 2017 (8 pgs.).
Case No. PRG2015-00011 Exhibit 1026 Deposition Transcript of Gojko Lalic, Ph.D. (Apr. 12, 2016)—Petitioner's Reply to Patent Owner's Response dated May 6, 2017 (79 pgs.).
Case No. PRG2015-00011 Exhibit 1031 Transmittal letter from M. Sawaya to L. McBluett (Mar. 26, 2014)—Petitioner's Reply to Patent Owner's Response dated May 6, 2017 (1 pg.).
Case No. PRG2015-00011 Exhibit 1032 Declaration No. 2 of Michael Sawaya (May 4, 2016)—Petitioner's Reply to Patent Owner's Response dated May 6, 2017 (3 pgs.).
Case No. PRG2015-00011 Exhibit 1033 Email from L. McBluett to M. Sawaya (Mar. 25, 2014)—Petitioner's Reply to Patent Owner's Response dated May 6, 2017 (1 pg.).
Case No. PRG2015-00011 Exhibit 1034 Deposition Transcript of Sailaja Machiraju (Apr. 29, 2016)—Petitioner's Reply to Patent Owner's Response dated May 6, 2017 (90 pgs.).
Case No. PRG2015-00011 Exhibit 1035 Orange Book listing for U.S. Pat. No. 8,859,623 (Accessed May 4, 2016)—Petitioner's Reply to Patent Owner's Response dated May 6, 2017 (5 pgs.).
Case No. PRG2015-00011 Exhibit 2001 Declaration of Assad Sawaya in Support of Altaire Pharmaceuticals, Inc. and Sawaya Aquebogue, LLC's Motion to Dismiss or, in the Alternative, for Transfer of Venue; *Paragon BioTeck, Inc.* v. *Altaire Pharmaceuticals, Inc. and Sawaya Aquebogue, LLC.* (Case 3:15-cv-00189-PK; Document 21; Filed Mar. 23, 2015; U.S. District Court of OR)—Redacted Patent Owner's Preliminary Response Pursuant to 37 C.F.R. § 42.207 dated Feb. 10, 2016 (10 pgs.).
Case No. PRG2015-00011 Exhibit 2002 Proof of Service Summons and Complaint; *Paragon BioTeck, Inc.* v. *Altaire Pharmaceuticals, Inc., et al* (Case 3:15-cv-00189-PK; Document 17; Filed Mar. 20, 2015; U.S. District Court of OR)—Redacted Patent Owner's Preliminary Response Pursuant to 37 C.F.R. § 42.207 dated Feb. 10, 2016 (3 pgs.).
Case No. PRG2015-00011 Exhibit 2003 Proof of Service Summons and Complaint; *Paragon BioTeck, Inc.* v. *Altaire Pharmaceuticals, Inc., et al* (Case 3:15-cv-00189-PK; Document 18; Filed Mar. 20, 2015; U.S. District Court of OR)—Redacted Patent Owner's Preliminary Response Pursuant to 37 C.F.R. § 42.207 dated Feb. 10, 2016 (3 pgs.).
Case No. PRG2015-00011 Exhibit 2004 Redacted Paragon's Response to Defendants' Motion to Dismiss or for Transfer of Venue; *Paragon BioTeck, Inc.* v. *Altaire Pharmaceuticals, Inc. and Sawaya Aquebogue, LLC.* (Case 3:15-cv-00189-PK; Document 27; Filed Apr. 15, 2015; U.S. District Court of OR)—Redacted Patent Owner's Preliminary Response Pursuant to 37 C.F.R. § 42.207 dated Feb. 10, 2016 (24 pgs.).
Case No. PRG2015-00011 Exhibit 2005 Air State Facility Permit Under the Environmental Conservation Law Issued to Sawaya Aquebogue, LLC for an Altaire Pharmaceuticals Facility on behalf of Michael Sawaya, Altaire Pharmaceuticals; New York State Department of Environmental Conservation (Effective Date Apr. 27, 2010)—Redacted Patent Owner's Preliminary Response Pursuant to 37 C.F.R. § 42.207 dated Feb. 10, 2016 (24 pgs.).
Case No. PRG2015-00011 Exhibit 2006 Altaire Pharmaceuticals, Inc. and Sawaya Aquebogue, LLC's Motion to Dismiss or, in the Alternative, for Transfer of Venue. *Paragon BioTeck, Inc.* v. *Altaire Pharmaceuticals, Inc. and Sawaya Aquebogue, LLC.* (Case 3:15-cv-00189-PK; Document 20; Filed Mar. 23, 2015; U.S. District Court of OR)—Redacted Patent Owner's Preliminary Response Pursuant to 37 C.F.R. § 42.207 dated Feb. 10, 2016 (28 pgs.).
Case No. PRG2015-00011 Exhibit 2008 USP Monographs: Phenylephrine Hydrochloride Injection, Pharmacopeia online, http://uspbpep.com/usp31/v31261/usp31nf26s1_m64170.asp#usp31nf26s1_m64170s3 (last visited Aug. 11, 2015)—Redacted Patent Owner's Preliminary Response Pursuant to 37 C.F.R. § 42.207 dated Feb. 10, 2016 (1 pg.).

(56) References Cited

OTHER PUBLICATIONS

Case No. PRG2015-00011 Exhibit 2009 USP Monographs: Phenylephrine Hydrochloride Nasal Jelly, Pharmacopeia online, http://uspbpep.com/usp031/v31261/usp31nf26s1_m64180.asp (last visited Aug. 11, 2015)—Redacted Patent Owner's Preliminary Response Pursuant to 37 C.F.R. § 42.207 dated Feb. 10, 2016 (1 pg.).
Case No. PRG2015-00011 Exhibit 2010 USP: General Chapters:< 621>Chromatography, U.S. Pharmacopeia, http://www.pharmacopeia.cn/v29240/usp29nf24s0_c621_viewall.html (last visited Aug. 24, 2015)—Redacted Patent Owner's Preliminary Response Pursuant to 37 C.F.R. § 42.207 dated Feb. 10, 2016 (26 pgs.).
Case No. PRG2015-00011 Exhibit 2011 USP: General Chapters:< 1225> Validation of Compendial Methods, U.S. Pharmacopeia, http://pharmacopeia.cn/v29240/usp29nf24s0_c1225.html (last visited Aug. 24, 2015)—Redacted Patent Owner's Preliminary Response Pursuant to 37 C.F.R. § 42.207 dated Feb. 10, 2016 (7 pgs.).
Case No. PRG2015-00011 Exhibit 2014 Paragon's Analysis of R-Phenylephrine Solutions Using Currently Published USP Methods (dated Oct. 11, 2013; Oct. 17, 2013 and Oct. 18, 2013—Redacted Patent Owner's Preliminary Response Pursuant to 37 C.F.R. § 42.207 dated Feb. 10, 2016 (7 pgs.).
Case No. PRG2015-00011 Exhibit 2015 Paragon BioTeck, Inc.'s Answer, Affirmative Defenses, Counterclaims, and Third-Party Complaint; *Altaire Pharmaceuticals, Inc.* v. *Paragon BioTeck, Inc.; Paragon BioTeck, Inc.* v. *Sawaya Aquebogue, LLC.* (Case 2:15-cv-02416-LDW-AYS; Document 22; Filed Aug. 14, 15; U.S. District Court of NY—Redacted Patent Owner's Preliminary Response Pursuant to 37 C.F.R. § 42.207 dated Feb. 10, 2016 (28 pgs.).
Case No. PRG2015-00011 Exhibit 2018 USP reference standard certificate for phenylephrine LOT M0L504 (2012)—Redacted Patent Owner's Preliminary Response Pursuant to 37 C.F.R. § 42.207 dated Feb. 10, 2016 (2 pgs.).
Case No. PRG2015-00011 Exhibit 2020 USP Monographs: Phenylephrine Hydrochloride, U.S. Pharmacopeia, http://www.pharmacopeia.cn/v29240/usp29nf24s0_m64160.html (last visited Jan. 4, 2016)—Redacted Patent Owner's Preliminary Response Pursuant to 37 C.F.R. § 42.207 dated Feb. 10, 2016 (3 pgs.).
Akorn, Inc. package insert for phenylephrine hydrochloride solution/drops, at http://dailymed.nlm.nih.gov/dailymed/lookup.cfm?setid=c5c51d8b-b50b-4c77-9d55-f64c14b0dOe5 (revised Sep. 2011).
Brown et al. Activities of octopamine and synephrine stereoisomers on a-adrenoceptors. Br. J. Pharmacol. 93:417-429 (1988).
Case No. PRG2015-00011 Exhibit 1022 Redacted Declaration of Assad Sawaya in Support of Petitioner's Reply dated Sep. 28, 2015—Redacted Reply to Patent Owner's Preliminary Statement dated Sep. 28, 2015 (6 pgs.).
Case No. PRG2015-00011 Exhibit 1023 Letter to Honorable Leonard D. Wexler. *Altaire Pharms., Inc.* v. *Paragon BioTeck, Inc.*, No. 2:15-cv-02416 (E.D.N.Y. Sep. 18, 2015)—Redacted Reply to Patent Owner's Preliminary Statement dated Sep. 28, 2015 (4 pgs.).
Case No. PRG2015-00011 Exhibit 1036 Email from A. Brown to D. Doshi et al. (Apr. 8, 2016)—Petitioner's Reply to Patent Owner's Response dated May 6, 2017 (1 pg.).
Case No. PRG2015-00011 Exhibit 2007 Letter from Michael Sawaya, General Counsel of Altaire Pharmaceuticals, Inc. to Travis Sydow of Paragon BioTeck, Inc. Dated Jun. 12, 2015 Redacted Patent Owner's Preliminary Response Pursuant to 37 C.F.R. 42.207 dated Feb. 10, 2016 (2 pgs.).
Case No. PRG2015-00011 Exhibit 2012 Protective Order in PGR2015-00011 Redacted Patent Owner's Preliminary Response Pursuant to 37 C.F.R. 42.207 dated Feb. 10, 2016 (9 pgs.).
Case No. PRG2015-00011 Exhibit 2013 Email from Roy Bryant to Patrick Witham and Lauren MC Bluett, Oct. 18, 2013 Redacted Patent Owner's Preliminary Response Pursuant to 37 C.F.R. 42.207 dated Feb. 10, 2016 (1 pg.).
Case No. PRG2015-00011 Exhibit 2016 Declaration of Dr. Gojko Lalic Redacted Patent Owner's Preliminary Response Pursuant to 37 C.F.R. 42.207 dated Feb. 10, 2016 (22 pgs.).
Case No. PRG2015-00011 Exhibit 2017 Curriculum vitae of Dr. Gojko Lalic Redacted Patent Owner's Preliminary Response Pursuant to 37 C.F.R. 42.207 dated Feb. 10, 2016 (7 pgs.).
Case No. PRG2015-00011 Exhibit 2019 Sigma-Aldrich® Product Specification for phenylephrine product No. P6126 Redacted Patent Owner's Preliminary Response Pursuant to 37 C.F.R. 42.207 dated Feb. 10, 2016 (1 pg.).
Case No. PRG2015-00011 Exhibit 2021 Declaration of Sailaja Machiraju Redacted Patent Owner's Preliminary Response Pursuant to 37 C.F.R. 42.207 dated Feb. 10, 2016 (7 pgs.).
Case No. PRG2015-00011 Exhibit 2022 Ernest L. Eliel et al., Stereochemistry of Organic Compounds (1994) Redacted Patent Owner's Preliminary Response Pursuant to 37 C.F.R. 42.207 dated Feb. 10, 2016 (25 pgs.).
Case No. PRG2015-00011 Exhibit 2024 Remington: The Science and Practice of Pharmacy, 21st Edition, Part 5: Pharmaceutical Manufacturing, p. 860 (Beringer et al. eds. 2006) Redacted Patent Owner's Preliminary Response Pursuant to 37 C.F.R. 42.207 dated Feb. 10, 2016 (4 pgs.).
Case No. PRG2015-00011 Exhibit 2027 ATCC, Product sheet for Pseudomonas aeruginosa (ATCC® 10145TM) (2015) Redacted Patent Owner's Preliminary Response Pursuant to 37 C.F.R. 42.207 dated Feb. 10, 2016 (2 pgs.).
Case No. PRG2015-00011 Exhibit 2030 Certificate of Incorporation of Altaire Pharmaceuticals, Inc. Redacted Patent Owner's Preliminary Response Pursuant to 37 C.F.R. 42.207 dated Feb. 10, 2016 (8 pgs.).
Case No. PRG2015-00011 Exhibit 2031 Articles of Organization of Sawaya Aquebogue, LLC Redacted Patent Owner's Preliminary Response Pursuant to 37 C.F.R. 42.207 dated Feb. 10, 2016 (7 pgs.).
Case No. PRG2015-00011 Exhibit 2032 Results of public records search for properties owned by Sawaya Aquebogue, LLC as of Jan. 22, 2016 Redacted Patent Owner's Preliminary Response Pursuant to 37 C.F.R. 42.207 dated Feb. 10, 2016 (2 pgs.).
Case No. PRG2015-00011 Exhibit 2034 Redacted Transcript of Assad Sawaya deposition, Jan. 20, 2016 Redacted Patent Owner's Preliminary Response Pursuant to 37 C.F.R. 42.207 dated Feb. 10, 2016 (82 pgs.).
Case No. PRG2015-00011 Exhibit 2035 Carol Lakkis et al., "Infection control guidelines for optometrists," Clin Exp Optom 90(6):434-444, 2007 Redacted Patent Owners Preliminary Response Pursuant to 37 C.F.R. 42.207 dated Feb. 10, 2016 (11 pgs).
Case No. PRG2015-00011 Exhibit 2036 Curriculum vitae of Sailaja Machiraju Redacted Patent Owner's Preliminary Response Pursuant to 37 C.F.R. 42.207 dated Feb. 10, 2016 (2 pgs.).
Case No. PRG2015-00011 Exhibit 2038 Sigma-Aldrich® Product Portfolio—Description of quality control tests performed on Sigma-Aldrich products according to quality grade (2010) Redacted Patent Owner's Preliminary Response Pursuant to 37 C.F.R. 42.207 dated Feb. 10, 2016 (2 pgs.).
Case No. PRG2015-00011 Notice of Deposition of Dr. Gojko Lalic dated Mar. 29, 2016 (3 pgs.).
Case No. PRG2015-00011 Notice of Deposition of Ms. Sailaja Machiruaju dated Apr. 15, 2016 (3 pgs.).
Case No. PRG2015-00011 Notice of Docketing dated Jan. 17, 2017 Case No. 17-1487—*Altaire Pharmaceuticals, Inc.* v. *Paragon Bioteck, Inc.* (1 pg.).
Case No. PRG2015-00011 Notice of Filing Date Accorded to Petition and Time for Filing Patent Owner Preliminary Response dated May 22, 2015 (Paper No. 3) (3 pgs.).
Case No. PRG2015-00011 Patent Owner Paragon Bioteck, Inc.'s Submission of Mandatory Notice Information Under 37 C.F.R. 42.8(a)(2) dated Jun. 1, 2015 (4 pgs.).
Case No. PRG2015-00011 Patent Owner's Mandatory Change-Of-Information Notices Under 37 C.F.R. 42.8(a)(3) dated Dec. 29, 2015 (4 pgs.).
Case No. PRG2015-00011 Patent Owner's Notice of Deposition of Assad Sawaya dated Jan. 7, 2016 (3 pgs).
Case No. PRG2015-00011 Petitioner's Notice of Appeal dated Jan. 13, 2017 (5 pgs.).
Case No. PRG2015-00011 Petitioner's Updated Mandatory Notices dated Feb. 18, 2016 (4 pgs.).

(56) References Cited

OTHER PUBLICATIONS

Case No. PRG2015-00011 Redacted Paragon's Opposition to Petitioner's Motion to Seal dated Mar. 7, 2016 (7 pgs.).
Case No. PRG2015-00011 Redacted Patent Owner's Response Pursuant to 37 C.F.R. 42.220 dated Feb. 10, 2016 (62 pgs.).
Case No. PRG2015-00011 Redacted Petitioner's Reply to Patent Owner's Response dated May 6, 2016 (32 pgs).
Case No. PRG2015-00011 Redacted Reply to Patent Owner's Preliminary Statement dated Sep. 28, 2015 (12 pgs.).
Chemical Abstracts Service "phenylephrine". CAS Registry No. 61-76-7 (1984).
El-Shibini et al. The Stability of Phenylephrine—Part 1: The Rate of Degradation of the Amino Group. Arzneimittelforschung 19(4):676-678 (1969) (w/ English translation).
El-Shibini et al. The Stability of Phenylephrine—Part 2: The discolouration reaction and the influence of some ions on the rate of degradation of the drug. Arzneimittelforschung 19(5):828-831 (1969) (w/English Translation).
El-Shibini et al. The Stability of Phenylephrine—Part 3: The racemisation reaction. Arzneimittelforschung 19(9):1613-1614 (1969) (w/English translation).
NDA 203510, Paragon BioTeck, Inc, p. 2-5, Revised Mar. 2013, p. 2, In3; p. 4, In20-22, 26-27; p. 5, In18-19, 24 http://www.accessdata.fda.gov/drugsatfda_docs/label/2013/203510s000lbl.pdf.
PCT/US2014/65496 International Preliminary Report on Patentability dated May 26, 2016.
PCT/US2014/65496 International Search Report and Written Opinion dated Jan. 27, 2015.
U.S. Appl. No. 14/080,771 Notice of Allowance dated Sep. 3, 2014.
U.S. Appl. No. 14/080,771 Office Action dated Feb. 4, 2014.
U.S. Appl. No. 14/080,771 Office Action dated Jun. 12, 2014.
U.S. Appl. No. 14/477,718 Office Action dated Apr. 14, 2016.
U.S. Appl. No. 14/477,718 Office Action dated Jul. 28, 2015.
Zaczek et al. The effect of phenylephrine on pain and flare intensity in eyes with uveitis. Acta Ophthalmol Scand 78(5):516-551 (2000).

\* cited by examiner

METHODS AND COMPOSITIONS OF STABLE PHENYLEPHRINE FORMULATIONS

CROSS-REFERENCE

This application is a continuation of U.S. patent application Ser. No. 15/625,624, filed Jun. 16, 2017, which is a continuation of U.S. patent application Ser. No. 14/477,718, filed Sep. 4, 2014, which is a continuation of U.S. patent application Ser. No. 14/080,771, filed Nov. 14, 2013, now U.S. Pat. No. 8,859,623, issued Oct. 14, 2014, all of which are hereby incorporated by reference in their entirety.

BACKGROUND OF THE INVENTION

Phenylephrine is a selective α1-adrenergic receptor agonist used primarily as a decongestant, as an agent to dilate the pupil, and to increase blood pressure. Phenylephrine is marketed as a substitute for the decongestant pseudoephedrine, though clinical studies differ regarding phenylephrine's effectiveness in this role.

SUMMARY OF THE INVENTION

In accordance with the present invention, the present invention provide a composition comprising at least 95% R-phenylephrine hydrochloride and an aqueous buffer, wherein the composition substantially maintains an initial chiral purity of R-phenylephrine hydrochloride for at least 6 months stored between −10 to 10 degree Celsius.

In another aspect, provided herein are methods of stabilizing a phenylephrine hydrochloride composition comprising storing a solution of aqueous R-phenylephrine hydrochloride at less than 10 degree Celsius, wherein the composition substantially maintains the initial chiral purity of R-phenylephrine hydrochloride for at least 6 months.

In one aspect, provided herein are methods of assaying chiral purity of R-phenylephrine hydrochloride, wherein the chiral purity is determined by chiral column chromatography, optical rotation, capillary electrophoresis, circular dichroism, or Nuclear Magnetic Resonance.

In another aspect provides compositions comprising R-phenylephrine hydrochloride, wherein the composition substantially maintains the initial chiral purity of R-phenylephrine hydrochloride for at least 6 months.

In another aspect provides methods of dilating the pupil comprising administering a composition comprising R-phenylephrine hydrochloride topically to a mammal, wherein the composition substantially maintains the initial chiral purity of R-phenylephrine hydrochloride for at least 6 months.

In another aspect provides methods of treating Uveitis in a subject comprising administering a composition comprising R-phenylephrine hydrochloride to said subject, wherein the composition substantially maintains the initial chiral purity of R-phenylephrine hydrochloride for at least 6 months In another aspect provides methods of performing certain ocular testing such as ultrasonography, provocative closed angle glaucoma test, Retinoscopy, compromised circulation (i.e., blanching test), Refraction, fundus examination comprising administering a composition comprising R-phenylephrine hydrochloride, wherein the composition substantially maintains the initial chiral purity of R-phenylephrine hydrochloride for at least 6 months.

In another aspect provides methods of aiding surgical procedures requiring visualization of the posterior chamber comprising administering a composition comprising R-phenylephrine hydrochloride to a subject, wherein the composition substantially maintains the initial chiral purity of R-phenylephrine hydrochloride for at least 6 months.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Phenylephrine differs chemically from epinephrine only in lacking one hydroxyl group (OH) in the four position on the benzene ring. It is a bitter-tasting crystalline material soluble in water and alcohols, with a melting point of 140°-145° C. Chemically it is Benzenemethanol, 3-hydroxy-α-[(methylamino)methyl]-, hydrochloride or (R)-(−)-m-hydroxy-α-[methylamino)methyl]benzyl alcohol hydrochloride with the following chemical structure.

It is known in the art that a Phenylephrine Hydrochloride solution should be stored protected from light. The benzylic hydrogen is acidic and can be deprotonated easily. The hydroxyl group may be oxidized to form a carbonyl moiety conjugated with phenyl group, especially with help of the adjacent basic amino group. Thus, it is known in the art that a Phenylephrine Hydrochloride solution should be stored protected from light. For example, an insert from a commercially available Phenylephrine Hydrochloride Ophthalmic Solution provides that the solution should be stored at 20° to 25° C. (USP controlled room temperature) and keep container tightly closed. Do not use if solution is brown or contains precipitate. (AKORN Package Insert)

However, a solution under such condition often turns brown over time despite of carefully keeping container tightly closed at 20° to 25° C. (USP controlled room temperature). Those packages containing the brown solution cannot be used and thus create waste.

The present invention provides the improvement to overcome such instability problem.

In some embodiments, there are provided a composition comprising at least 95% R-phenylephrine hydrochloride and an aqueous buffer for substantially maintaining chiral purity of R-phenylephrine hydrochloride for at least 6 months, the improvement comprising storing the composition between −10 to 10 degree Celsius. In certain embodiments, the composition is stored between 2 to 8 degree Celsius. In certain embodiments, the composition comprises at least 99% or 99.3%, R-phenylephrine hydrochloride. In certain embodiments, the chiral purity of R-phenylephrine hydrochloride is at least 95%, 97%, 99%, or 99.5% of the initial chiral purity after 6 months. In certain embodiments, the composition comprises 2.5% w/v or 10% w/v R-phenylephrine hydrochloride by weight. In certain embodiments, the composition further comprises a preservative such as benzalkonium chloride, stearalkonium chloride, polyaminopropyl biguanide, or the like. In some embodiments, the composition is in a 1-15 ml plastic or glass bottle. In some embodiments, the composition is in a glass or plastic bottle of about 2 ml, about 3 ml, about 5 ml, about 10 ml or about 15 ml. In certain embodiments, the plastic or glass bottle is opaque.

In some embodiments provide methods of stabilizing a phenylephrine hydrochloride composition such as a solution of aqueous R-phenylephrine hydrochloride at less than 10 degree Celsius wherein the composition substantially maintains the initial chiral purity of R-phenylephrine hydrochloride for at least 6 months.

In some embodiments provide herein compositions comprising R-phenylephrine hydrochloride, wherein the composition substantially maintains the initial chiral purity of R-phenylephrine hydrochloride for at least 6 months.

In some embodiments, the composition is stored at −10 to 10 degree Celsius. In certain embodiments, the composition is stored at −5 to 10 degree Celsius. In certain embodiments, the composition is stored at 0 to 10 degree Celsius. In certain embodiments, the composition is stored at 2 to 8 degree Celsius.

The term "substantial" or "substantially maintains" described herein refers to not more than 15% deviation of the initial purity. In some embodiments, the chiral purity of the composition is at least 85%, 90%, 95%, 97%, 99%, 99.1%, 99.2%, 99.3%, 99.4%, 99.5%, 99.6%, 99.7%, 99.8% or 99.9% of the initial chiral purity.

In some embodiments provide herein methods of assaying chiral purity of R-phenylephrine hydrochloride, wherein the chiral purity is determined by chiral column chromatography, optical rotation, capillary electrophoresis, circular dichroism, or Nuclear Magnetic Resonance.

In certain embodiments, the chiral purity is determined by chiral column chromatography.

Chiral Column Chromatography

Chiral column chromatography is a variant of column chromatography in which the stationary phase contains a single enantiomer of a chiral compound rather than being achiral. The two enantiomers of the same analyte compound differ in affinity to the single-enantiomer stationary phase and therefore they exit the column at different times.

The chiral stationary phase can be prepared by attaching a suitable chiral compound to the surface of an achiral support such as silica gel, which creates a Chiral Stationary Phase (CSP). Many common chiral stationary phases are based on oligosaccharides such as cellulose or cyclodextrin (in particular with β-cyclodextrin, a seven sugar ring molecule). As with all chromatographic methods, various stationary phases are particularly suited to specific types of analytes.

The packing material of the chiral column may be amylose tris(3,5-dimethylphenylcarbamate), β-cyclodextrin, cellobiohydrolase, selector R-(−)-N-(3,5-dinitrobenzoyl)-phenylglycine, cellulose tris(3,5-dimethylphenylcarbamate), cellulose tris(3,5-dichlorophenylcarbamate), or combinations thereof. In some embodiments, the chiral column for analytical purpose is packed with amylose tris(3,5-dichlorophenylcarbamate). The column may have a packing particle of a size of about 3 μm to about 50 μm. In some embodiments, the column has a packing particle a size of about 3 μm, 5 μm, 10 μm, 20 μm, 30 μm, 40 μm, or 50 μm. In certain embodiments, the column has a packing particle a size of about 3 In some embodiments, when using a chiral column system, the first mobile phase is non-polar solvent such as n-hexane, n-pentane, and the like, and the second mobile phase is polar solvent such as isopropanol, ethanol, methanol, or the like. In certainly embodiments, the mobile phase comprises small amount of amine such as ethylenediamine. The first mobile phase may be present in an amount of about 75% to about 95% by volume and the second mobile phase is present in an amount of about 5% to about 25% by volume. In some embodiments, the first mobile phase is present in an amount of about 85% by volume and the second mobile phase is present in an amount of about 15% by volume with or without ethylenediamine.

Other Chiral Compound Analysis Methods

There are several chiral compound purification and analysis methods available besides chiral column chromatography. For example, it is known in the art chiral purity can be determined by optical rotation. In some embodiments, the chiral purity of R-phenylephrine hydrochloride in the stabilized compositions and methods thereof can be determined by comparison of optical rotation of pure R-phenylephrine hydrochloride.

Optical Purity Measured by Optical Rotation

Molecules with chrial centers cause the rotation of plane polarised light and are said to be "optically active" (hence the term optical isomers). Enantiomeric molecules rotate the plane in opposite directions but with the same magnitude. This provides a means of measuring the "optical purity" or "enantiomeric excess (ee)" of a sample of a mixture of enantiomers.

Specific rotation is a physical property like boiling point and can be looked up in references. It is defined according to the following equation based on the experimental measurements: Specific rotation $[\alpha] = \alpha_{obs}/cl$ where "$\alpha_{obs}$" is the experimentally observed rotation, "c" is the concentration in g/ml and "l" is the path length of the cell used expressed in dm (10 cm).

A non-racemic mixture of two enantiomers will have a net optical rotation. It is possible to determine the specific rotation of the mixture and, with knowledge of the specific rotation of the pure enantiomer, the optical purity can be determined.

% Optical purity of sample=100*(specific rotation of sample)/(specific rotation of a pure enantiomer)

In some embodiments, there are provided methods of assaying chiral purity of R-phenylephrine hydrochloride, wherein the chiral purity is determined by optical rotation. In certain embodiments, the optical rotation is determined by comparison of optical rotation of pure R-phenylephrine hydrochloride.

Capillary Electrophoresis

Capillary electrophoresis (CE), also known as capillary zone electrophoresis (CZE), can be used to separate ionic species by their charge and frictional forces and hydrodynamic radius.

Capillary electrophoresis (CE) in general offers highly efficient separations. To achieve chiral separation, the capillary is filled with a separation buffer containing a chiral additive. Although many chiral selectors have been used successfully, the most comprehensive separation strategies have been achieved with highly sulfated cyclodextrins. In some embodiments, the chiral purity of the compositions provided herein is determined by capillary electrophoresis. In certain embodiments, the capillary electrophoresis uses cyclodextrin or its derivatives (such as sulfated cyclodextrins).

Chiral Purity Measured by Circular Dichroism

Circular dichroism (CD) refers to the differential absorption of left and right circularly polarized light. This phenomenon is exhibited in the absorption bands of optically active chiral molecules. CD spectroscopy has a wide range of applications in many different fields. For example, vibrational circular dichroism, which uses light from the infrared energy region, is used for structural studies of small organic molecules, and most recently proteins and DNA. In general, this phenomenon will be exhibited in absorption bands of any optically active molecule. As a consequence, circular dichroism is exhibited by biological molecules, because of their dextrorotary and levorotary components. Even more important is that a secondary structure will also impart a distinct CD to its respective molecules.

Optical rotation and circular dichroism stem from the same quantum mechanical phenomena and one can be derived mathematically from the other if all spectral information is provided. In some embodiments, the chiral purity is determined by circular dichroism. In certain embodiments, the chiral purity is determined by Fourier transform infrared vibrational circular dichroism (FTIR-VCD). A skilled person in the art can readily apply the general knowledge and procedure to determine chirality of the compositions provided herein.

NMR Spectroscopy of Stereoisomers

It is known in the art that NMR spectroscopy techniques can determine the absolute configuration of stereoisomers such as cis or trans alkenes, R or S enantiomers, and R,R or R,S diastereomers. In a mixture of enantiomers, these methods can help quantify the optical purity by integrating the area under the NMR peak corresponding to each stereoisomer. Accuracy of integration can be improved by inserting a chiral derivatizing agent with a nucleus other than hydrogen or carbon, then reading the heteronuclear NMR spectrum: for example fluorine-19 NMR or phosphorus-31 NMR. Mosher's acid contains a —CF3 group, so if the adduct has no other fluorine atoms, the 19F NMR of a racemic mixture shows just two peaks, one for each stereoisomer. In some embodiments, the chiral purity of the compositions provided herein is determined by Nuclear Magnetic Resonance Spectroscopy (NMR). In certain embodiments, a chirally pure complexing reagent (i.e., a chiral derivatizing agent) is used in measuring NMR. A skilled person in the art can readily utilize NMR and any suitable chiral complexing agent to determine the chirality of the compositions provided herein.

Dosage Forms and Strengths

In some embodiments, the stabilized compositions provided herein comprise a solution of 2.5% w/v or 10% w/v R-phenylephrine hydrochloride by weight. In certain embodiments, the compositions further comprise sodium phosphate monobasic, sodium phosphate dibasic, boric acid and benzalkonium chloride. The followings are non-limited exemplary compositions:

Phenylephrine Hydrochloride Ophthalmic Solution, 2.5% is a clear, colorless to yellowish, sterile topical ophthalmic solution containing phenylephrine hydrochloride 2.5%.

Phenylephrine Hydrochloride Ophthalmic Solution, 10% is a clear, colorless to yellowish, sterile topical ophthalmic solution containing phenylephrine hydrochloride 10%.

Application of the Stabilized Compositions Comprising R-Phenylephrine Hydrochloride It has been established that Phenylephrine Hydrochloride Ophthalmic Solution is recommended as a vasoconstrictor, decongestant, and mydriatic in a variety of ophthalmic conditions and procedures. Some of its uses are for pupillary dilation in uveitis (to prevent or aid in the disruption of posterior synechia formation), for many ophthalmic surgical procedures and for refraction without cycloplegia. Phenylephrine Hydrochloride Ophthalmic Solution may also be used for funduscopy and other diagnostic procedures.

For example, R-Phenylephrine is used to dilate the iris through α-adrenergic stimulation of the iris dilator muscle. Sympathetic stimulation of the ciliary muscle is believed to be inhibitory, decreasing accommodative amplitude. R-Phenylephrine is formulated in an eye drop to dilate the pupil in order to facilitate visualization of the retina. It is often used in combination with tropicamide as a synergist when tropicamide alone is not sufficient. Surprisingly it was found that S-Phenylephrine dilated the eye only slightly more than that was untreated. Thus it is important that an eye drop containing Phenylephrine Hydrochloride used for dilation of the pupil contains predominantly the R-isomer in order to maintain maximum efficacy of the ophthalmic solution.

Sympathetic innervation leads to pupillary dilation. It is innervated by the sympathetic system, which acts by releasing noradrenaline, which acts on α1-receptors causing dilation.

The alpha-1 ($\alpha_1$) adrenergic receptor is a G protein-coupled receptor (GPCR) associated with the $G_q$ heterotrimeric G-protein. It consists of three highly homologous subtypes, including $\alpha_{1A}$-, $\alpha_{1B}$-, and $\alpha_{1D}$-adrenergic. Catecholamines like norepinephrine (noradrenaline) and epinephrine (adrenaline) signal through the $\alpha_1$-adrenergic receptor in the central and peripheral nervous systems.

Phenylephrine is a selective $\alpha_1$-adrenergic receptor agonist used primarily as a decongestant, as an agent to dilate the pupil, and to increase blood pressure. Dilation is controlled by the dilator pupillae, a group of muscles in the peripheral ⅔ of the iris. Sympathetic innervation begins at the cortex with the first synapse at the cilliospinal center (also known as Budge's center after German physiologist Julius Ludwig Budge). Post synaptic neurons travel down all the way through the brain stem and finally exit through the cervical sympathetic chain and the superior cervical ganglion. They synapse at the superior cervical ganglion where third-order neurons travel through the carotid plexus and enter into the orbit through the first division of the trigeminal nerve.

In the anesthetized rats, infusion of large amount of (+)-epinephrine, (+)-norepinephrine, epinine, and (−)- or (+)-phenylephrine induces tachyphylaxis to vasopressor effect of (−)-epinephrine, (−)-norepinephrine, and tetraethylammonium. The tachyphylactic potency of the amines was (−)-phenylephrine (R-phenylephrine)>epinine>(+)-norepinephrine=(+)-epinephrine>(+)-phenylephrine.

Two ophthalmic formulations, formulated 10% Phenylephrine hydrochloride (S-isomer) and the exemplary invention composition, 10% Phenylephrine hydrochloride (R-isomer) were tested for their ocular activity in NZW rabbits. It was observed that formulated S-isomer showed minimal dilation, responded to light exposure and constricted slightly more slowly than the untreated eye, where as the exemplary invention composition, 10% Phenylephrine hydrochloride showed maximal dilation with in 15 min of dosing and the pupil did not respond to light and remained dilated for 4 hrs.

According to the above study it could be postulated that, when an ophthalmic solution of phenylephrine hydrochloride, (R-isomer) containing S-isomer as an impurity is used for dilation of pupil, the s-isomer may cause the saturation of the a-adrenergic receptors resulting in the decrease in the response of the drug after its administration (tachyphylasis). Furthermore, the presence of S-isomer in the ophthalmic solution may lead to poor/delayed dilation of the pupil.

In some embodiments provide methods of dilating the pupil comprising administering a composition comprising R-phenylephrine hydrochloride topically to a mammal, wherein the composition substantially maintains the initial chiral purity of R-phenylephrine hydrochloride for at least 6 months. It is evident from the literature that the pharmacological evaluation of both R & S-Phenylephrine hydrochloride is not same. R-Phenylephrine is referenced as useful synthetic adrenergic drug.

Uveitis

Uveitis is, broadly, inflammation of the uvea. The uvea consists of the middle, pigmented, vascular structures of the eye and includes the iris, ciliary body, and choroid. Uveitis requires an urgent referral and thorough examination by an ophthalmologist or Optometrist and urgent treatment to control the inflammation. Anterior uveitis (iritis) affects the front portion of the eye, intermediate uveitis (cyclitis) affects the ciliary body, and posterior uveitis (choroiditis) affects the back portion of the uvea. Diffuse uveitis affects all portions of the uvea. Anterior uveitis commonly occurs in conjunction with juvenile rheumatoid arthritis, but does not manifest in all juvenile arthritis patients. Uveitis is most likely to be present in juvenile arthritis patients with pauciarticular disease (fewer than five joints involved), a positive anti-nuclear antibody test, and a negative rheumatoid factor test. It has been demonstrated that after phenylephrine hydrochloride ophthalmic solution instillation, flare intensity and pain were significantly decreased only in eyes with iridocyclitis and without fibrinoid reaction (FR). The decreasing level of flare intensity, and paralysis of the pupil after phenylephrine instillation seem to alleviate pain in those eyes. See e.g., Zaczek, et. al., Acta Ophthalmol Scand. 2000 October; 78(5):516-8.

In some embodiments provide methods of treating Uveitis in a subject comprising administering a composition comprising R-phenylephrine hydrochloride to said subject, wherein the composition substantially maintains the initial chiral purity of R-phenylephrine hydrochloride for at least 6 months.

In some embodiments provide methods of performing certain ocular testing such as ultrasonography, provocative closed angle glaucoma test, Retinoscopy, compromised circulation (i.e., blanching test), Refraction, fundus examination comprising administering a composition comprising R-phenylephrine hydrochloride, wherein the composition substantially maintains the initial chiral purity of R-phenylephrine hydrochloride for at least 6 months.

In some embodiments provide methods of aiding surgical procedures requiring visualization of the posterior chamber comprising administering a composition comprising R-phenylephrine hydrochloride, wherein the composition substantially maintains the initial chiral purity of R-phenylephrine hydrochloride for at least 6 months.

After presentation of R-phenylephrine hydrochloride ophthalmic solution 2.5% or 10% to the ocular surface, a broad variation in the delay of onset of dilation is widely reported, varying between 20-to-30 minutes and as much as up to 60 minutes. While a number of contributors to this delay of onset have been theorized, the absence of phenylephrine hydrochloride's pharmacologic activity in the eye due to the presence of S-phenylephrine may in fact be the explanation for such delay.

Dropper Bottle or Storage Bottle

Conventional dropper bottles for administering ophthalmic fluid are well known in the prior art. The basic commercial design of such dropper bottles has remained fairly unchanged over the last several decades: a squeezable container is provided with a tapered dispenser that terminates in a discharge aperture. To administer ophthalmic fluid, the discharge aperture is aligned above a target eye and the bottle is squeezed to urge out a drop or dose of the fluid.

Alternatively, liquid dispensers have been developed in which the formulation is supplied from a storage bottle through a dropper, for example (dropper bottles or EDO-Ophthiols). The aqueous formulation usually flows out of the dropper opening as a result of manual pressure being applied to the compressible storage bottle.

In some embodiments, the composition described herein is stored in a plastic or glass bottle. In certain embodiments, the plastic bottle is a low-density polyethylene bottle. In certain embodiments, the composition described herein is stored in a glass bottle with or without a liquid dispenser. In certain embodiments, the plastic or glass bottle is opaque.

Additionally, the compositions described herein are either packaged for single use or for multiple uses with or without a preservative.

Certain Pharmaceutical and Medical Terminology

The term "acceptable" with respect to a formulation, composition or ingredient, as used herein, means having no persistent detrimental effect on the general health of the subject being treated.

The term "carrier," as used herein, refers to relatively nontoxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery.

Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

All of the various embodiments or options described herein can be combined in any and all variations. The following Examples serve only to illustrate the invention and are not to be construed in anyway to limit the invention.

EXAMPLES

Example 1. Exemplary Phenylephrine HCl Ophthalmic Formulation

R-Phenylephrine Hydrochloride Ophthalmic Solution, USP 2.5% or 10%, is a sterile, clear, colorless to light yellow, topical mydriatic agent for ophthalmic use. The chemical name is (R)-3-hydroxy-α-[(methylamino)methyl] benzenemethanol hydrochloride. R-Phenylephrine hydrochloride is represented by the following structural formula:

Phenylephrine hydrochloride has a molecular weight of 203.67 and an empirical formula of $C_9H_{13}NO_2$—HCl.

Each mL of R-Phenylephrine Hydrochloride Ophthalmic Solution, 2.5% contains: ACTIVE: phenylephrine hydrochloride 25 mg (2.5%); INACTIVES: sodium phosphate monobasic, sodium phosphate dibasic; boric acid, water for injection. Hydrochloric acid and/or sodium hydroxide may be added to adjust pH (6.0 to 6.4). The solution has a tonicity of 500 mOsm/kg; PRESERVATIVE: benzalkonium chloride 0.01%.

Each mL of R-Phenylephrine Hydrochloride Ophthalmic Solution, 10% contains: ACTIVE: R-phenylephrine hydrochloride 100 mg (10%); INACTIVES: sodium phosphate monobasic, sodium phosphate dibasic; water for injection. Hydrochloric acid and/or sodium hydroxide may be added to adjust pH (6.3 to 6.7). The solution has a tonicity of 1000 mOsm/kg; PRESERVATIVE: benzalkonium chloride 0.01%.

The composition of Phenylephrine HCl Ophthalmic Solution, 2.5% and 10% is listed in Table 1.

TABLE 1

Phenylephrine HCl Ophthalmic Solution, 2.5% and 10% Quantitative Composition

| Component | 2.5% Formulation Quantity (% w/v) | 10% Formulation Quantity (% w/v) | Function | Quality Standard |
|---|---|---|---|---|
| R-Phenylephrine HCl | 2.5% | 10% | Active Ingredient | USP |
| Sodium Phosphate Monobasic, Anhydrous | 0.5% | 0.5% | Buffer | USP |
| Sodium Phosphate Dibasic, Anhydrous | 0.3% | 0.3% | Buffer | USP |
| Boric Acid | 1.0% | | Buffer | USP |
| Benzalkonium Chloride | 0.01% | 0.01% | Anti-microbial preservative | USP |
| Sodium Hydroxide | As needed | As needed | pH adjustment | USP |
| Hydrochloric Acid | As needed | As needed | pH adjustment | USP |

Example 2. Stability (Impurity) Test and Results

Stability studies of 2.5% and 10% Phenylephrine HCL solutions prepared as in Example 2 were conducted at 2 to 8° C. for 12 months.

While the testing performed during the historical stability analysis is limited, those parameters evaluated show excellent results. For the 3 batches of 2.5% formulation evaluated, the initial assay averaged 101.2% of label claim (range 99.8%-102.9%), and after 12 months of storage at the labeled storage condition (2-8° C.) the average potency was 99.7% of label claim (range 97.0%-103.4%). All other parameters evaluated (appearance, preservative effectiveness, sterility) conformed to specifications.

For the 3 batches of 10% formulation evaluated, the initial assay averaged 100.4% of label claim (range 99.8%-101.6%), and after 12 months of storage at the labeled storage condition (2-8° C.) the average potency was 99.8% of label claim (range 98.8%-101.0%). All other parameters evaluated (appearance, preservative effectiveness, sterility) conformed to specifications.

Example 3. Chiral HPLC Analysis

The following are non-limited exemplary chiral columns and relevant mobile phases in the methods for analyzing chiral purity of R-phenylephrine.

Column-OJ-RH (150×4.6) mm, 5 μm, Flow: 1 mL min-1, Mobile Phase: Methanol, Column Temp: 25° C., Detection wavelength: 270 nm.

Column-OJ-RH (150×4.6) mm, 5 μm, Flow: 0.8 mL min-1, Mobile Phase: 0.05% Ethylenediamine in Methanol, Column Temp: 25° C., Detection wavelength: 270 nm.

Column-OJ-RH (150×4.6) mm, Flow: 1 ml min-1, Mobile Phase: 0.05% Ethylenediamine in Methanol, Column Temp: Ambient, Detection wavelength: 270 nm.

Column-OJ-RH (150×4.6) mm, 5 μm, Flow: 1 ml min-1, Mobile Phase: 0.05% Ethylenediamine in Methanol, Column Temp: 25° C., Detection wavelength: 270 nm.

Column-OJ-RH (150×4.6) mm, 5 μm, Flow: 1 ml min-1, Mobile Phase: 0.05 Ethylenediamine in Methanol, Column Temp: 25° C., Detection wavelength: 270 nm.

Column-OJ-RH (150×4.6) mm, 5 μm, Flow: 1 ml min-1, Mobile Phase: 0.05% Ethylenediamine in Water (05%): Methanol (95), Column Temp: 25° C., Detection wavelength: 270 nm.

Column-OJ-RH (150×4.6) mm, 5 μm, Flow: 1 ml min-1, Mobile Phase: 0.05% Ethylenediamine in Methanol, Column Temp: 25° C., Detection wavelength: 270 nm.

Column-OJ-RH (150×4.6) mm, 5 μm, Flow: 1 ml min-1, Mobile Phase: 0.05% Ethylenediamine in Methanol, Column Temp: 25° C., Detection wavelength: 270 nm.

Column-OJ-RH (150×4.6) mm, 5 μm, Flow: 0.5 ml min-1, Mobile Phase: Acetonitrile: 0.05% Ethylenediamine in water (30:70) Column Temp.: 25° C., Detection wavelength: 270 nm.

Column-OJ-RH (150×4.6) mm, 5 μm, Flow: 0.5 ml min-1; Mobile Phase: Acetonitrile: 0.05% Ethylenediamine in water (40:60) Column Temp.: 25, Detection wavelength: 270 nm.

Column-Chiralpak IC-3 (150×4.6) mm, 3 μm, Flow: 1.0 ml min-1, Mobile Phase: 0.1% Ethylenediamine in n-Hexane (85%):Ethanol (15%), Column Temp: 25° C., Detection wavelength: 270 nm; ref 600 nm.

Column-Chiralpak IC-3 (150×4.6) mm, 3 μm, Flow: 1.2 ml min-1, Mobile Phase: 0.1% Ethylenediamine in n-Hexane (50%):IPA (50%), Column Temp: 25° C., Detection wavelength: 270 nm.

Figure 1:
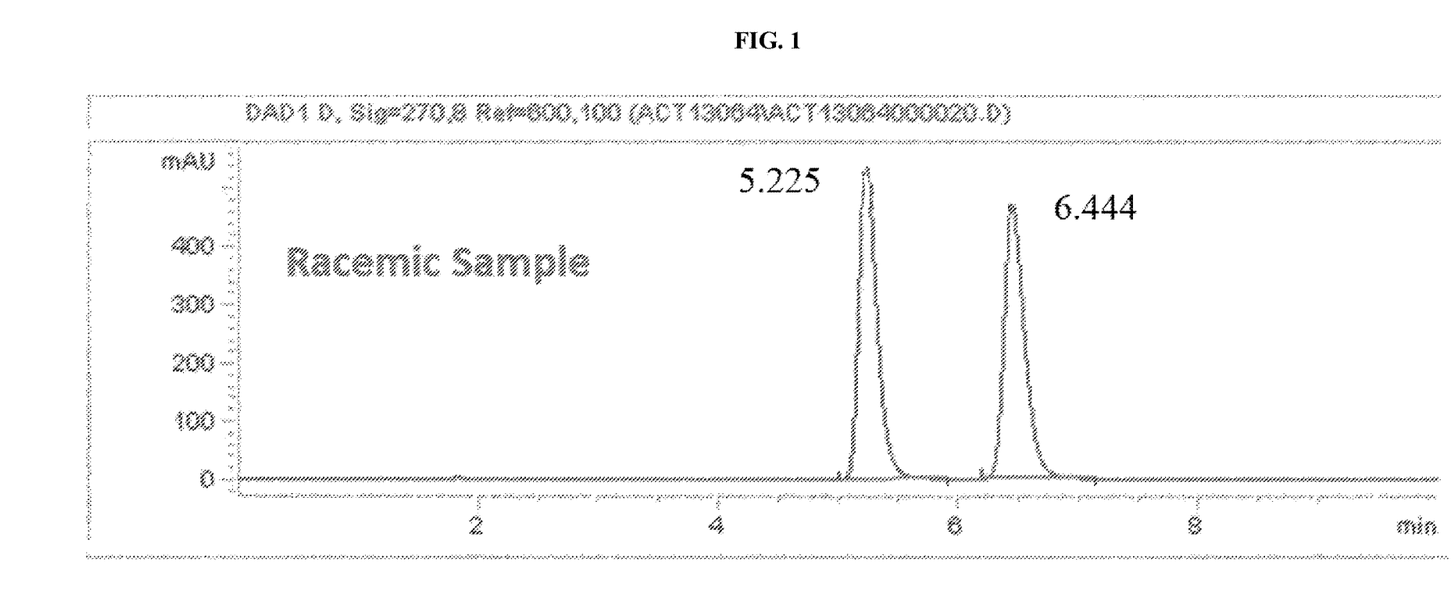
FIG. 1 shows a HPLC chromatogram of racemic R-phenylephrine hydrochloride by a chiral column purification (OJ-RH (150×4.6) mm). Two peaks at the retention time 5.225 minutes and 6.444 minutes are shown.

Column-OJ-RH (150×4.6) mm, Flow: 0.6 ml min-1, Mobile Phase: 0.05% Ethylenediamine in Methanol, Column Temp: 25° C.; Detection wavelength: 270 nm. 4.0 mg sample in 1 mL ethanol was analyzed. The injection volume to HPLC is 3.0 μL. The HPLC chromatogram is shown in FIG. 1.

The HPLC chromatogram clearly show separation of racemic sample. Chiral HPLC method was thus established to analyze Phenylephrine.

Figure 2:
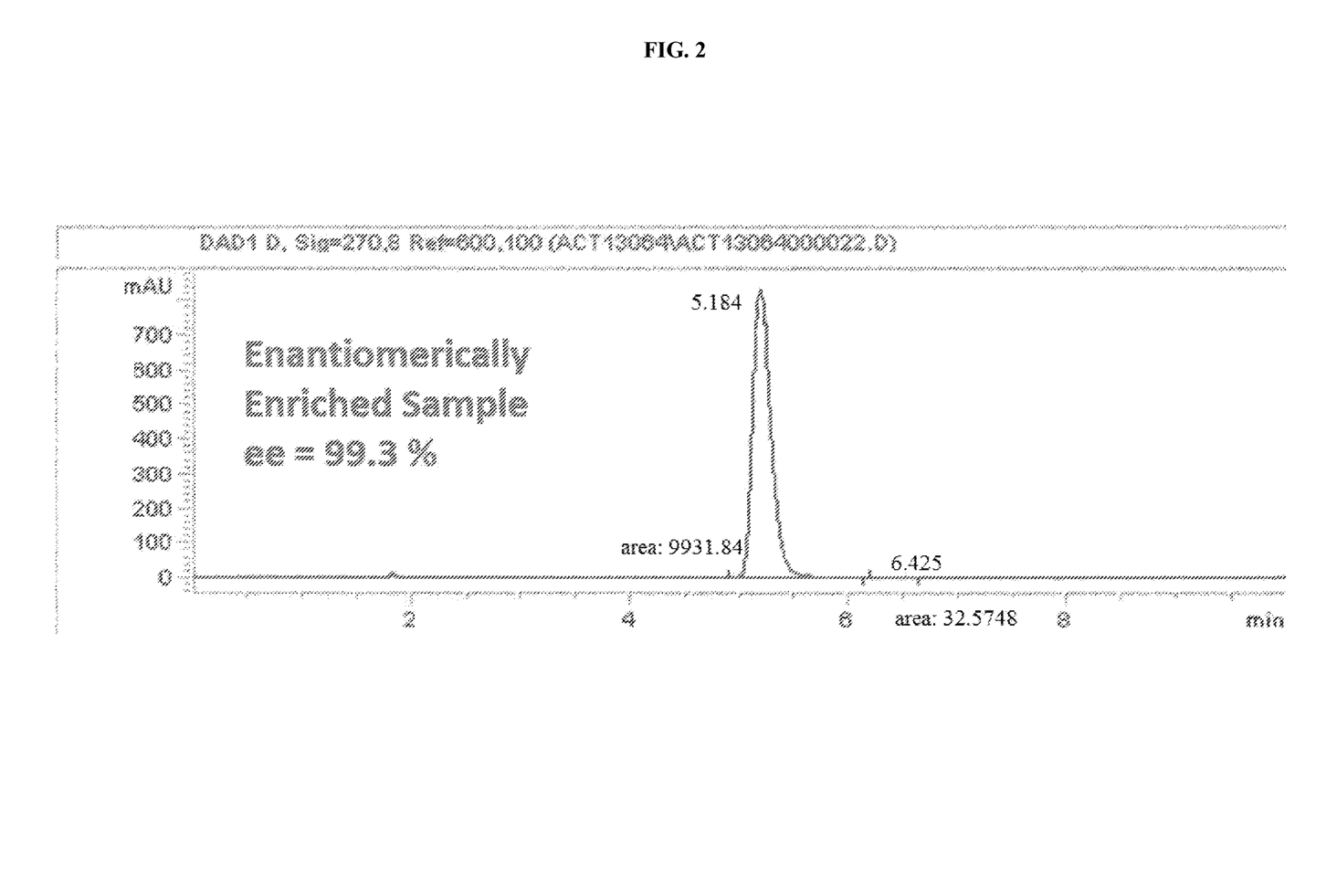
FIG. 2 shows a HPLC chromatogram of the exemplary R-Phenylephrine Hydrochloride Opthalmic Solution (10%) before storage. The chiral purity was determined to be 99.3% ee based on the peaks at 5.184 minutes (area: 9931.84) and at 6.425 minutes (area: 32.5748).

Example 4. Determination of Chiral Purity after 6 Months Storage at Low Temperature R-Phenylephrine Hydrochloride Opthalmic Solution, 2.5% and 10% prepared as in Example 1 were stored at 2 to 8° C. The chiral purity of Sample 1 (10% solution) was assessed before low temperature stability test. The HPLC chromatogram is shown in FIG. 2.

The chiral purity of R-Phenylephrine Hydrochloride was determined by the method and conditions as shown in Example 3. The result showed 99.3% ee.

Figure 3:
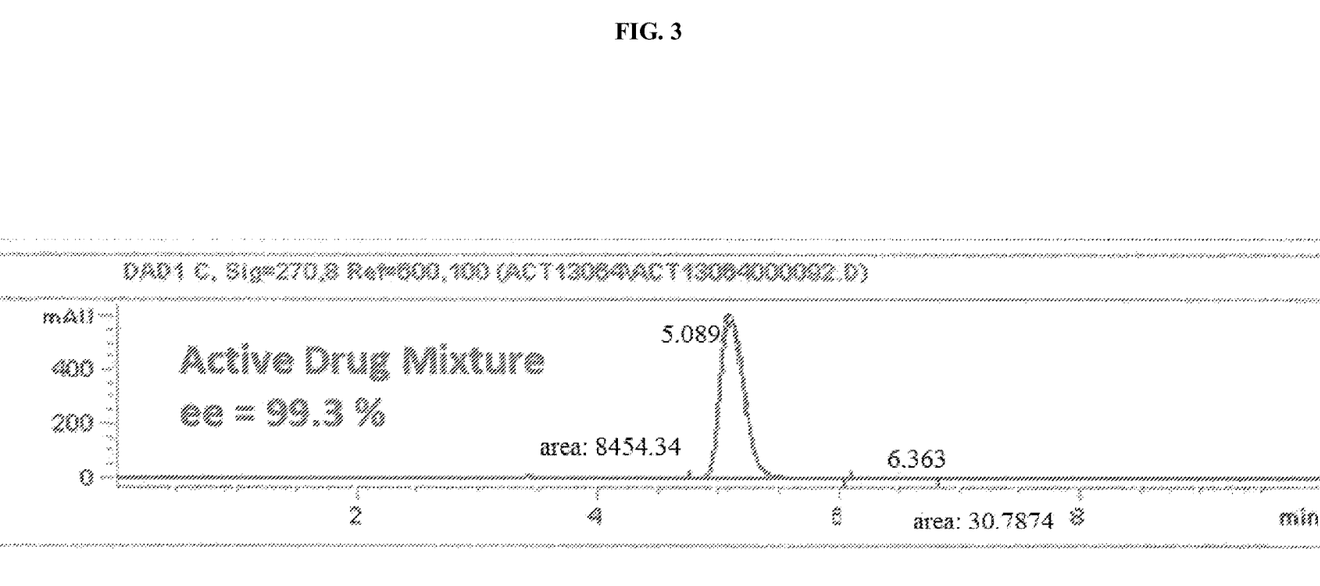
FIG. 3 shows a HPLC chromatogram of the exemplary R-Phenylephrine Hydrochloride Opthalmic Solution (10%) stored at 2 to 8° C. after 6 months. The chiral purity was determined to be 99.3% ee based on the peaks at 5.089 minutes (area: 8454.34) and at 6.363 minutes (area: 30.7874).

After 6 months of low temperature storage (i.e., 2 to 8° C.), the chiral purity of R-Phenylephrine Hydrochloride in the solution was determined to be 99.3% ee. The HPLC chromatogram is shown in FIG. 3.

Figure 4:
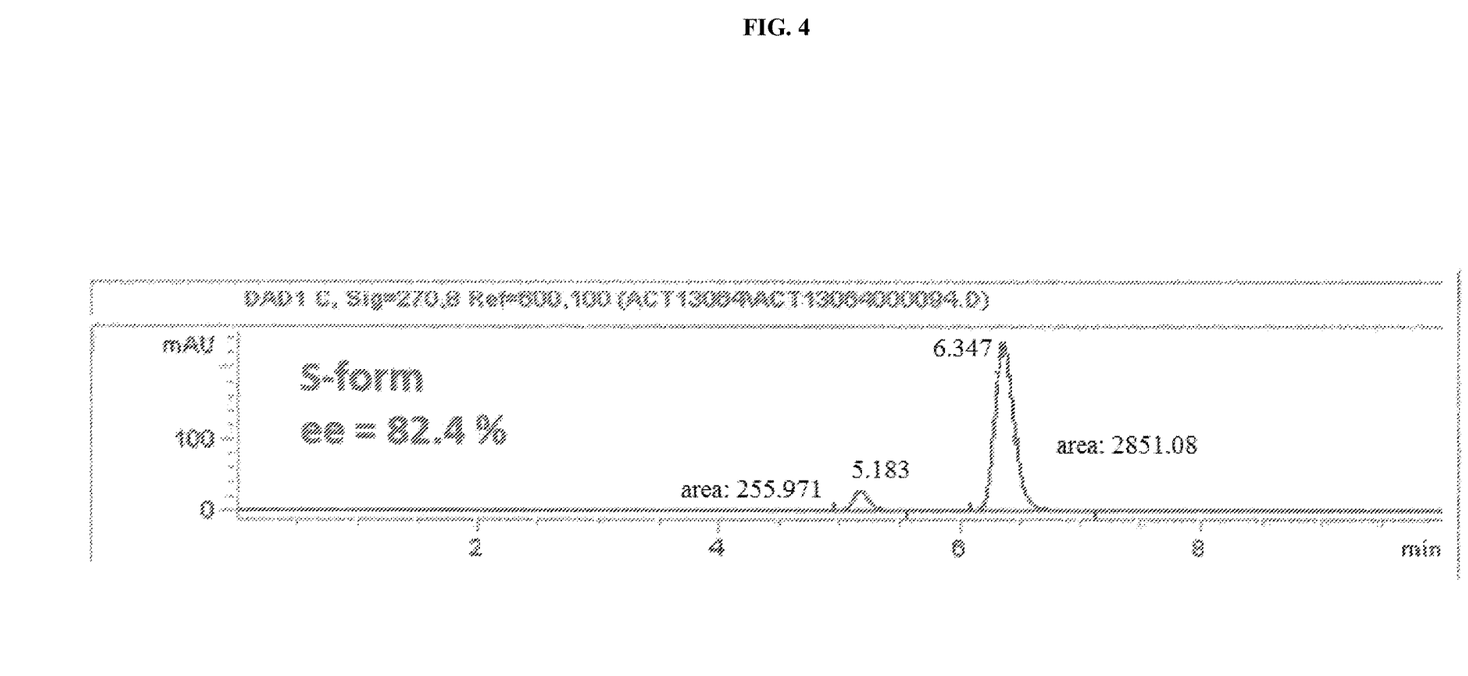
FIG. 4 shows a HPLC chromatogram of the purified "impurity" which is a S-Phenylephrine Hydrochloride. The chiral purity was determined to be 82.4% ee based on the peaks at 5.183 minutes (area: 255.971) and at 6.347 minutes (area: 2851.08).

To confirm the "impurity" shown in the chromatogram, the "impurity" was purified and determined by the same method. The "impurity" (i.e., S-Phenylephrine Hydrochloride) was determined to possess 82.4% ee of S-form. The HPLC chromatogram is shown in FIG. 4.

Thus, it is clearly shown that the solution remain substantially maintains the initial chiral purity of R-phenylephrine hydrochloride for at least 6 months.

Example 5. Dilation Assay of S Form Phenylephrine Solution

Both R and S form solutions (10% solution prepared as in Example 1) were test for dilation on rabbits. The first test rabbit received 3 drops of the S form formulation and the second test rabbit received 3 drops of the R form solution.

The results were as follows:

Test Rabbit No. 1: Minimal Dilation, within 15 minutes of dilation the pupil was only slightly more dilated than the untreated eye. The treated eye responded to light exposure and constricted slowly. The control eye constricted rapidly as was expected.

Test Rabbit No 2: Maximal dilation within 15 minutes of dosing. The pupil did not respond to light exposure and remained fully dilated for 4 hours then regressed.

These results clearly show that an ophthalmic solution of phenylephrine containing S-isomer does not dilate the rabbit pupil as it is achieved with an ophthalmic solution of phenylephrine containing R isomer. Thus it is evident that maintaining the chiral purity of the ophthalmic solution is crucial to keep drug potency.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of dilating a pupil of a subject in need thereof, the method comprising storing a comprising R-phenylephrine hydrochloride and an aqueous buffer at a temperature between −10 to 10 degree Celsius prior to use and subsequently administering the composition to an eye of the subject, wherein the composition has a pH of from about 6.0 to about 6.7 when stored prior to administration, and wherein the composition comprises R-phenylephrine hydrochloride having an initial chiral purity of at least 95% enantiomeric excess (ee) as determined by chiral column chromatography at a time prior to storage and a chiral purity of at least 95% (ee) as determined by chiral chromatography at the time of use after storage when administered to the pupil of the subject, and wherein storing the composition at a temperature between −10 to 10 degrees Celsium maintains the chiral purity of at least 95% (ee) as determined by chiral column chromatography for a period of at least 6 months storage.

2. The method of claim 1, wherein the pupil attains maximal dilation with about 15 minutes of administration.

3. The composition of claim 1, wherein the composition comprises R-phenylephrine hydrochloride with an initial chiral purity of at least 99% (ee) as determined by chiral column chromatography.

4. The method of claim 1, wherein the composition comprises R-phenylephrine hydrochloride with an initial chiral purity of at least 99.5% (ee) as determined by chiral column chromatography.

5. The method of claim 1, wherein the composition comprises 2.5% w/v or 10% w/v R-phenylephrine hydrochloride by weight.

6. The method of claim 1, wherein the pupil remains dilated for about 4 hours.

7. The method of claim 1, wherein the subject has uveitis.

8. The method of claim 7, wherein the uveitis is anterior uveitis (iritis), intermediate uveitis (cyclitis), and posterior uveitis (choroiditis), or diffuse uveitis.

9. The method of claim 1, wherein the aqueous buffer comprises sodium phosphate monobasic and sodium phosphate diabasic.

10. The method of claim 1, wherein the chiral column chromatography uses a column packing material selected from amylose tris(3,5-dimethylphenylcarbamate), β-cyclodextrin, cellobiohydrolase, selector R-(−)-N-(3,5-dinitrobenzoyl)-phenylglycine, cellulose tris(3,5-dimethylphenylcarbamate), cellulose tris(3,5-dichlorophenylcarbamate), or a combination thereof.

11. The method of claim 10, wherein the column packing material is amylose tris(3,5-dichlorophenylcarbamate).

12. The method of claim 10, wherein the chiral purity of R-phenylephrine hydrochloride is analyzed using Column-OJ-RH (150×4.6) mm, flow; 0.6 ml min-1, mobile phase: 0.05% ethylenediamine in methanol, column temperature: 25° C., and detection wavelength: 270 nm.

13. The method of claim 12, wherein chiral purity is determined based on chromatogram peaks at about 5.0 to about 5.2 minutes for R-phenylephrine hydrochloride and at about 6.3 to about 6.4 minutes for S-phenylephrine hydrochloride.

14. The method of claim 1, wherein the aqueous buffer comprises sodium phosphate monobasic, sodium phosphate dibasic, and boric acid.

15. The method of claim 1, wherein the composition comprises 2.5% w/v R-phenylephrine hydrochloride by weight, and wherein the composition has a pH of from about 6.0 to about 6.4.

16. The method of claim 1, wherein the composition comprises 10% w/v R-phenylephrine hydrochloride by weight, and wherein the composition has a pH of from about 6.3 to about 6.7.

17. The method of claim 1, wherein the composition is stored at temperature of 2 to 8 degree Celsius prior to administration.

18. The method of claim 2, further comprising performing ocular testing in the eye of the subject after administering the composition, wherein the ocular testing is selected from the groups consisting of ultrasonography, provocative closed angle glaucoma test, retinoscopy, blanching test, refraction, and fundus examination.

* * * * *